(12) United States Patent
Fukuda et al.

(10) Patent No.: US 9,042,517 B2
(45) Date of Patent: May 26, 2015

(54) X-RAY IMAGING APPARATUS

(75) Inventors: Kazunori Fukuda, Fujisawa (JP);
Kazuhiro Takada, Kawasaki (JP);
Taihei Mukaide, Yokohama (JP);
Masatoshi Watanabe, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 233 days.

(21) Appl. No.: 13/643,260

(22) PCT Filed: Apr. 19, 2011

(86) PCT No.: PCT/JP2011/060009
§ 371 (c)(1),
(2), (4) Date: Oct. 24, 2012

(87) PCT Pub. No.: WO2011/136157
PCT Pub. Date: Nov. 3, 2011

(65) Prior Publication Data
US 2013/0039466 A1    Feb. 14, 2013

(30) Foreign Application Priority Data

Apr. 27, 2010    (JP) .................................. 2010-102527

(51) Int. Cl.
*G01N 23/04*    (2006.01)

(52) U.S. Cl.
CPC ........ *G01N 23/046* (2013.01); *G01N 2223/419* (2013.01)

(58) Field of Classification Search
CPC ........ A61B 6/484; A61B 6/032; G01N 23/06; G21K 2207/005; G21K 1/10
USPC .......................... 378/62, 53; 702/28, 172, 189
See application file for complete search history.

(56) References Cited

U.S. PATENT DOCUMENTS

| 8,214,158 B2* | 7/2012 | Mukaide et al. ................. 702/28 |
| 2007/0064868 A1* | 3/2007 | Kostka et al. .................... 378/53 |

(Continued)

FOREIGN PATENT DOCUMENTS

| JP | 10509075 A | 9/1998 |
| JP | 2001099790 A | 4/2001 |

(Continued)

OTHER PUBLICATIONS

Kagoshima, et al., "Scanning Differential-Phase-Contrast Hard X-Ray Microscopy with Wedge Absorber Detector", Japanese Journal of Applied Physics, Oct. 15, 2004, pp. 1449-1451, vol. 43, No. 11A.

(Continued)

*Primary Examiner* — Michael Maskell
(74) *Attorney, Agent, or Firm* — Canon USA Inc. IP Division

(57) ABSTRACT

To provide an X-ray imaging apparatus capable of easily adjusting the sensitivity or capable of easily extracting the amount of refraction of X-rays.
An X-ray imaging apparatus irradiating an object to be measured with an X-ray beam from an X-ray source that generates X-rays of a first energy and X-rays of a second energy different from the first energy to measure an image of the object to be measured includes an attenuator and a detector. The attenuator attenuates the X-ray beam transmitted through the object to be measured and is configured so as to vary the amount of attenuation of the X-rays depending on a position on which the X-ray beam is incident. The detector detects the X-ray beam transmitted through the attenuator and is configured so as to detect the X-rays of the first energy and the second energy.

15 Claims, 7 Drawing Sheets

(56) References Cited

U.S. PATENT DOCUMENTS

| | | | |
|---|---|---|---|
| 2010/0189218 A1* | 7/2010 | Sakaguchi et al. | 378/62 |
| 2010/0318302 A1* | 12/2010 | Mukaide et al. | 702/28 |
| 2011/0158389 A1* | 6/2011 | Mukaide et al. | 378/62 |
| 2012/0294421 A1* | 11/2012 | Mukaide et al. | 378/62 |

FOREIGN PATENT DOCUMENTS

| | | |
|---|---|---|
| JP | 2004-008460 A | 1/2004 |
| JP | 2005278880 A | 10/2005 |
| JP | 2007-271468 A | 10/2007 |
| JP | 2009-192519 A | 8/2009 |
| JP | 2009258102 A | 11/2009 |
| JP | 2010-502977 A | 1/2010 |
| JP | 2011011039 A | 1/2011 |
| JP | 2011022134 A | 2/2011 |
| JP | 2011041795 A | 3/2011 |
| JP | 2011125668 A | 6/2011 |
| JP | 2011125669 A | 6/2011 |

OTHER PUBLICATIONS

Mukaide, et al., "Scanning hard x-ray differential phase contrast imaging with a double wedge absorber", Review of Scientific Instruments, (2009), pp. 033707-1-033707-5, vol. 80.

* cited by examiner

X-RAY IMAGING APPARATUS

TECHNICAL FIELD

The present invention relates to an X-ray imaging apparatus.

BACKGROUND ART

X-ray imaging apparatuses taking X-ray transmittance images are used in various fields of industrial and medical fields because the apparatuses can be used to non-destructively visualize the internal structures of objects to be measured (hereinafter referred to as objects). The contrast of an X-ray transmission image is caused by the differences in transmittance among X-rays transmitted through parts of an object. The transmittance of X-ray depends on the chemical composition of objects, the density of the objects, and the energies of the X-rays (i.e. the wavelength of the X-rays) that are used. Accordingly, in the case of using an X-ray apparatuses in related art, it is difficult to take legible high-contrast images of objects, such as soft materials or biological objects, mainly composed of light elements or fabricated by the objects and surrounding materials whose densities have small differences, because the objects have very high or similar X-ray transmittance.

X-ray imaging methods for detecting phase differences among X-rays are proposed (for example, refer to NPL 1) in order to measure high-contrast images of such objects. The phase difference appears as refraction in a portion having a density difference, for example, on an interface of a substance. In the method described in NPL 1, an object is irradiated by highly monochromatic X-rays and the intensity of the X-rays transmitted through the object is detected with an X-ray wedge-shaped attenuator. Specifically, the change in the amount of refraction angle of the X-rays through the object is detected as the change in the detected intensity to detect the phase difference in the method described in NPL 1. Since phase information on the X-rays (the amount of refraction of the X-rays) can be detected with the method described in NPL 1, it is possible to measure an image of high contrast.

CITATION LIST

Non Patent Literature

NPL 1 Yasushi KAGOSHIMA, "Scanning Differential-Phase-Contrast Hard X-Ray Microscopy with Wedge Absorber Detector", Japanese Journal of Applied Physics, Vol. 43, No. 11A, 2004, pp. L1449-L1451

SUMMARY OF INVENTION

Technical Problem

Since the monochromatic X-rays are used in the method described in NPL 1, it is not possible to easily adjust the sensitivity of the X-ray imaging apparatus.

In addition, with the method described in NPL 1, the detected intensity of the X-rays is varied depending on absorption and refraction of the X-rays through the object unless the absorption of the X-rays through the object is negligibly small. Accordingly, it is necessary to extract the contribution in detected intensities due to the refraction (the amount of refraction of the X-rays) from the result of detection.

The present invention provides an X-ray imaging apparatus capable of easily adjusting the sensitivity or an X-ray imaging apparatus capable of easily extracting the amount of refraction of X-rays.

Solution to Problem

According to an embodiment of the present invention, an X-ray imaging apparatus measures an X-ray transmittance image of the object by irradiating an X-ray beam from an X-ray source generating X-rays of a first energy and of a second energy different from the first energy to the object. This apparatus includes an attenuator configured to attenuate the X-ray beam transmitted through the object to be measured; and a detector configured to detect the X-ray beam transmitted through the attenuator. The attenuator is configured so as to vary an amount of attenuation of the X-rays depending on a position on which the X-ray beam is incident. The detector is configured so as to detect the X-rays of the first energy and of the second energy.

"The X-ray source generating the X-rays of the first energy and of the second energy" includes an X-ray source generating X-rays of other energies, in addition to the X-rays of the first energy and of the second energy. Similarly, "the detector detecting the X-rays of the first energy and of the second energy" includes a detector detecting X-rays of other energies, in addition to the X-rays of the first and the second energy.

Advantageous Effects of Invention

According to the present invention, it is possible to provide an X-ray imaging apparatus capable of easily adjusting the sensitivity or an X-ray imaging apparatus capable of easily extract the amount of refraction of X-rays.

DESCRIPTION OF EMBODIMENTS

Figure 1:
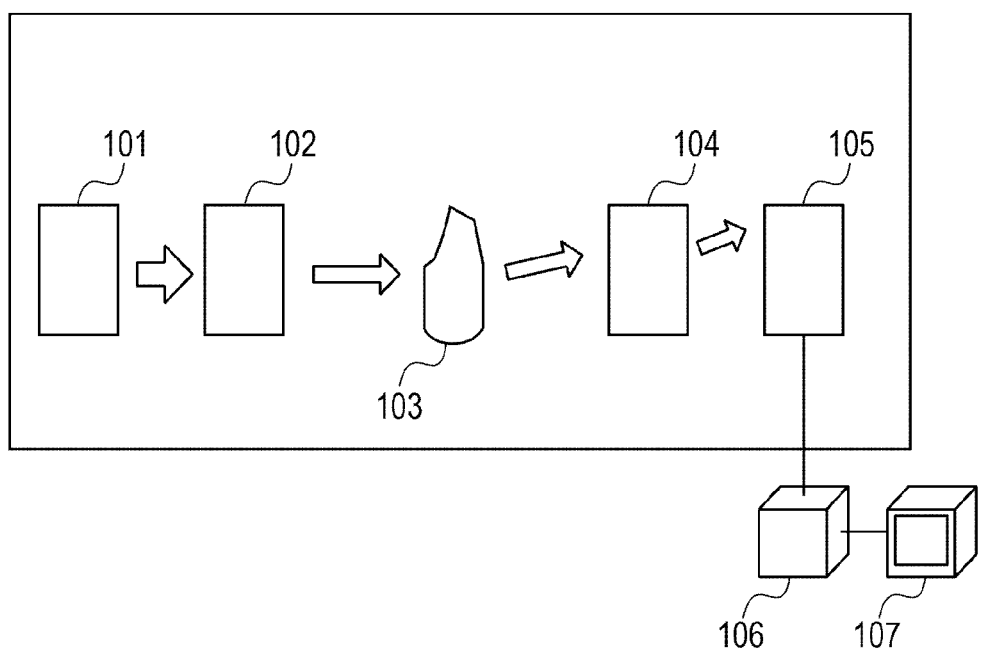
FIG. 1 schematically illustrates an X-ray imaging apparatus according to an embodiment of the present invention.

Embodiments of the present invention will herein be described in detail with reference to the attached drawings. The same reference numerals are used in the drawings to identify the same components. A duplicated description of such components is omitted herein.

An X-ray imaging apparatus according to an embodiment of the present invention will now be described with reference to FIGS. 1 to 3B. FIG. 1 schematically illustrates the X-ray imaging apparatus of the present embodiment. In the X-ray imaging apparatus of the present embodiment, an object to be measured is irradiated with X-rays generated from an X-ray source to measure an image of the object. The X-ray imaging apparatus of the present embodiment includes an irradiation unit, a stage (not shown) on which an object to be measured (hereinafter referred to as an object) 103 is placed, an X-ray attenuator 104, an X-ray detector 105, and a computer (control unit). The irradiation unit includes an X-ray source 101 and an aperture 102 serving as an X-ray adjuster. The computer includes a computing machine 106 serving as a calculating unit and a display 107 serving as a display unit. Arrows in FIG. 1 represent X-rays.

The X-ray source 101 is capable of generating X-rays of at least two different energies. (That is, the X-ray source 101 is capable of generating X-rays of a first energy and a second energy. The X-ray source 101 may generate X-rays of a third energy or, of a third energy and a fourth energy, in addition to the X-rays of the first and second energies. The difference between the first energy and the second energy is preferably higher than the energy resolution of the X-ray detector 105.) For example, a synchrotron radiation source having continuous X-ray energy spectrum or an X-ray tube may be used as the X-ray source 101. An X-ray tube capable of producing bremsstrahlung X-rays, at least two kinds of characteristic X-rays, or bremsstrahlung X-rays and at least one kind of characteristic X-rays may be used as the X-ray tube. The X-rays are electromagnetic waves having wavelength of about 0.01 angstroms to 100 angstroms ($10^{-12}$ m to $10^{-8}$ m). X-rays of shorter wavelengths ($\lambda$=0.01 angstroms to 1 angstrom) are called hard X-rays and X-rays of longer wavelengths ($\lambda$=1 angstrom to 100 angstroms) are called soft X-rays.

The X-ray adjuster 102 adjusts the cross-sectional shapes of the X-rays which are generated from the X-ray source 101 and with which the object is irradiated, and is capable of spatially limiting or dividing the X-rays. The X-ray adjuster 102 is configured by providing an aperture in a shield plate made of an absorbing material, such as a heavy metal, shielding the X-rays or sufficiently absorbing the X-rays to fulfill the purpose. The aperture may have a slit shape or a pin-hole shape. Alternatively, multiple slit-shaped or pin-hole-shaped apertures may be arranged. An X-ray beam adjusted by the X-ray adjuster 102 is subjected to absorption and refraction through the object 103 and is incident on the X-ray attenuator 104.

The X-ray attenuator 104 is configured so as to vary the amount of attenuation of the X-rays depending on the position of incident X-ray beam. Accordingly, the amount of X-rays transmitted through the X-ray attenuator 104 is varied depending on the positional shift of the optical path of the X-rays caused by the refraction through the object 103. "The amount of attenuation of X-rays is varied depending on the position of incident X-rays" means in this description that the amount of attenuation of the X-rays (the amount of change in intensity of the X-rays) is varied depending on the position of incident X-rays "at least one direction." The X-ray attenuator 104 will be specifically described below.

It is sufficient for the X-ray detector 105 to have sensitivity to the X-rays of the first energy and the second energy. The X-ray detector 105 is more preferably capable of detecting the X-ray spectrum distribution of the X-rays and capable of detecting the intensity of X-rays of each energy. The calculating unit 106 calculates physical quantities concerning the object 103 from information on the energies and the intensities of the X-rays detected by the X-ray detector 105. The display unit 107 appropriately displays the physical quantities calculated by the calculating unit 106. An X-ray spectroscope, such as a semiconductor detector, capable of detecting the spectrum distribution of X-rays may be used as the X-ray detector 105. For example, a silicon drift detector may be used as the semiconductor detector.

The object 103 is provided on the stage (not shown) serving as a movement mechanism. Even if only one X-ray beam is formed by the X-ray adjuster 102, moving the object 103 on the stage to scan the object 103 with the X-ray beam allows the whole area of the object 103 to be measured.

The X-ray beam is refracted when the density, shape, or chemical composition of the object 103 is varied on a surface or inner structure of the object 103. Accordingly, the presence of the object 103 causes the optical path of the X-ray beam to be shifted. The shift depends on a change in density, shape, or chemical composition of the object, the energies of incident X-rays, and so on.

Provided that $I_0$ denotes the intensity of an X-ray beam from the X-ray adjuster 102 and the chemical composition of the object 103 is constant for simplicity, an intensity $I_1$ of the X-ray beam transmitted through the object 103 is expressed by Equation (1):

$$I_1(E,d)=I_0(E)\cdot\exp\{-t(E)/l_{es}(E,d)\} \quad (1)$$

In Equation (1), t denotes the optical path length of the X-rays transmitted through the object 103, $l_{es}$ denotes the attenuation length of the X-rays with respect to the object 103, in which the exponent term denotes the transmittance of the X-rays with respect to the object 103, E denotes the energy of the X-rays, and d denotes the density of the object 103. $\Delta\theta$ denotes an amount of refraction angle through the object 103 and it is expressed by Equation (2):

$$\Delta\theta(E,d)=\Delta(\delta(E,d)t(E)) \quad (2)$$

In Equation (2), $\delta$ denotes the shift from 1 of the refraction index of a material composing the object 103 with respect to the X-rays. $\delta$ is expressed by Equation (3):

$$\delta(E,d)=(r_e\lambda^2/2\pi)Nf(E) \quad (3)$$

In Equation (3), $r_e$ denotes a classical electron radius, $\lambda$ denotes the wavelength of the X-rays, N denotes the number of atoms per unit volume, and f denotes an atomic scattering factor. When the object 103 is composed of various kinds of atoms, Nf is calculated by adding up the numbers N of the various kinds of atoms per unit volume. Since $\lambda$ has reciprocal relationship with the energy E and N has linear relationship with the density d, the amount of refraction is increased with the decreasing energy E and with the increasing density d.

Figure 2A:
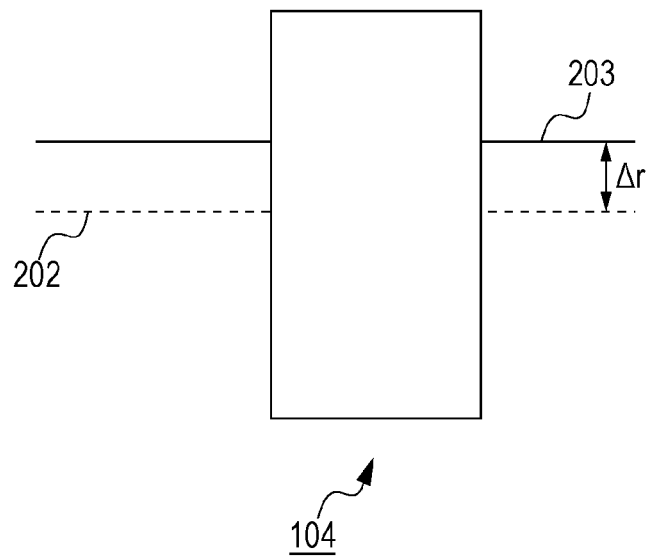
FIG. 2A schematically illustrates an X-ray attenuator in FIG. 1.

FIG. 2A schematically illustrates the X-ray attenuator 104. At the position of the X-ray attenuator 104, a positional shift $\Delta r$ occurs between an optical path 203 of the X-ray beam refracted through the object 103 and an optical path 202 of the X-ray beam when the object 103 does not exist on the optical path.

Figure 2B:
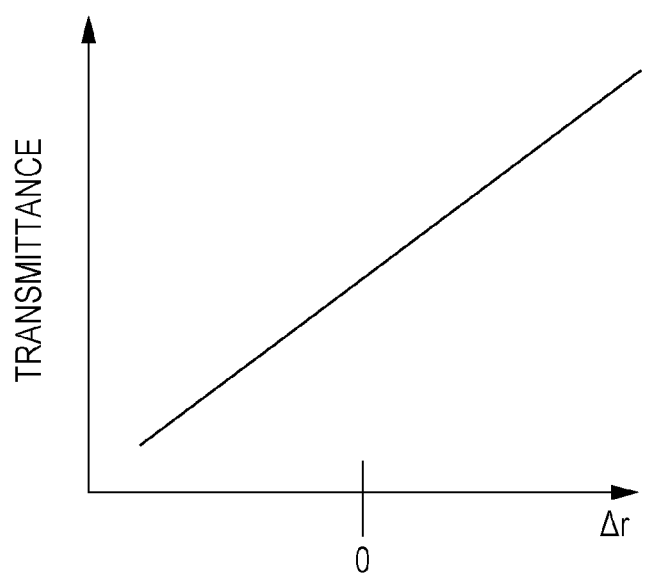
FIG. 2B shows an example of the transmittance of the X-ray attenuator in FIG. 2A.

FIG. 2B shows an example of the transmittance of the X-ray attenuator 104 with respect to the positional shift $\Delta r$. The X-ray attenuator 104 is configured so as to vary the transmittance with the positional shift $\Delta r$.

Calculation performed by the calculating unit 106 will now be described. When the function shown in FIG. 2B is denoted by PF, an intensity $I_2$ of the X-ray beam transmitted through the X-ray attenuator 104, detected by the X-ray detector 105, is expressed by Equation (4):

$$I_2(E,d) = I_0(E) \cdot \exp\{-t(E)/l_{es}(E,d)\} PF(\Delta r) \quad (4)$$

Accordingly, the positional shift $\Delta r$ is expressed by Equation (5):

$$\Delta r = PF^{-1}(I_2(E,d)/\{I_0(E) \cdot \exp(-t(E)/l_{es}(E,d))\}) \quad (5)$$

where $PF^{-1}$ denotes an inverse function of the function PF.

The amount $\Delta\theta$ of refraction angle of X-rays through the object 103 is expressed by Equation (6). An amount $\Delta\phi$ of phase shift of X-rays is calculated according to Equation (7).

$$\Delta\theta = \tan^{-1}(\Delta r/L) \quad (6)$$

$$\Delta\phi = (2\pi/\lambda)\Delta\theta \quad (7)$$

where L denotes the distance between the object 103 and the X-ray attenuator 104.

If the absorption through the object 103 is negligibly small, the term of the transmittance (exponent term) through the object 103 in Equation (4) is equal to one. Accordingly, it is possible to uniquely determine the positional shift $\Delta r$ from Equation (5) even when monochromatic X-rays are used. The amounts $\Delta\theta$ and $\Delta\phi$ are calculated from Equations (6) and (7), respectively, by using the determined positional shift $\Delta r$.

When the monochromatic X-rays are used as in the method described in NPL 1, any one of the distance L, the shape of the X-ray attenuator 104, and the material of the X-ray attenuator 104 can be changed to vary the sensitivity of the transmitted X-ray beam with respect to the positional shift. In contrast, the X-ray imaging apparatus of the present embodiment uses the X-ray source generating X-rays of multiple energies and the X-ray detector detecting the X-rays of multiple energies. The X-ray detector has an energy resolution sufficient to discriminately detect the intensity of the X-rays of each of multiple energies. The amount of refraction of the X-rays transmitted through the object is varied with the energies of the X-rays. Consequently, with the X-ray imaging apparatus of the present embodiment, it is possible to vary the sensitivity of the transmitted X-ray with respect to the positional shift by changing the energy of the X-ray beam used in the calculating unit.

If the absorption through the object 103 is not negligible, the term of the transmittance through the object 103 in Equation (4) is not equal to one. Accordingly, it is not possible to uniquely determine the positional shift $\Delta r$ from Equation (5) when the monochromatic X-ray is used. In contrast, since the X-ray imaging apparatus of the present embodiment uses the X-rays of multiple energies for measurement, Equation (5) is given for the X-ray of each energy. In addition, since the amount of refraction of the X-rays through the object 103 is minute and the change in the optical path length in response to the change in the energy E is substantially negligible except for cases in which the change in density is very large, t(E) is constant regardless of the energy. Accordingly, it is possible to calculate $\Delta r(E)$, t (corresponding to the thickness of the object), and d by measuring $I_2(E,d)$ for two or more energies E and using Equation (5). The calculation of $\Delta r(E)$ allows phase information including the amount of refraction and the amount of phase shift to be calculated from Equations (6) and (7). The detection sensitivity of the X-ray imaging apparatus can be easily varied in a manner described below. Specifically, the use of $I_2(E)$ for a lower energy E in the calculation of the above physical quantities allows conditions to increase $\Delta r(E)$ for the same object 103, thereby increasing the sensitivity.

As described above, according to the X-ray imaging apparatus of the present embodiment, it is possible to easily adjust the sensitivity to the positional shift of the optical path of the X-ray beam. In addition, it is possible to easily extract the amount of refraction of the X-rays through the object 103 with the X-ray imaging apparatus of the present embodiment even if the absorption of the X ray through the object 103 is not negligible. Furthermore, it is possible to generate the X-rays of two or more energies with the X-ray source 101 and to simultaneously detect the intensities of the X-rays of two or more energies with the X-ray detector 105 in the X-ray imaging apparatus of the present embodiment. In other words, with the X-ray imaging apparatus of the present embodiment, it is possible to simultaneously measure $I_2(E)$ for two or more energies E and there is no need to separately measure the amount of absorption.

An element in which above-mentioned attenuators are arranged in a line form or in a two-dimensional array form may be used as the X-ray attenuator used in the present embodiment. The element is configured so as to vary the amount of attenuation of the X-rays depending on position of the incident X-ray beam in each attenuator. Such an element may be considered as an X-ray attenuator array.

Similarly, any X-ray detector having the sensitivity to the X-rays of the first energy and the second energy may be used as the X-ray detector used in the present embodiment. Accordingly, an X-ray detector in which a fluorescent substance converting the X-rays into fluorescence having lower energies is combined with a photodetector capable of detecting the fluorescence may be used as the X-ray detector. In this case, a charge coupled device (CCD) image sensor or a complementary metal oxide semiconductor (CMOS) image sensor made of single crystal silicon may be used as the photodetector. Alternatively, a flat panel image sensor, made of thin non-single crystal silicon, may be used as the photodetector.

The attenuators in the X-ray attenuator array described above may be associated with the pixels in the image sensor in one-to-one, one-to-many, or many-to-one relationship in spatial arrangement.

First Embodiment

An X-ray imaging apparatus according to a first embodiment of the present invention will now be described with reference to FIGS. 3A and 3B.

A rotating anode X-ray tube made of molybdenum is used as the X-ray source 101 in the first embodiment. Two apertures each having spatial size of 50 μm×50 μm are used as the X-ray adjuster 102. In the X-ray adjuster 102, the shield plate is made of tantalum. The two apertures are arranged along the optical path, and the cross-sectional size of X-ray beam is limited to a certain value by the X-ray adjuster.

Figure 3A:
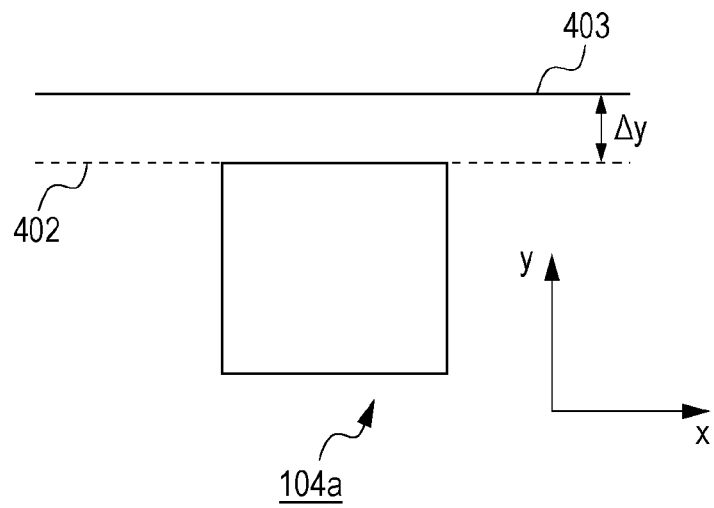
FIG. 3A schematically illustrates an X-ray attenuator according to a first embodiment of the present invention.

FIG. 3A shows an example of the cross-sectional shape of an X-ray attenuator 104a in the first embodiment. The X-ray attenuator 104a shown in FIG. 3A has a square pillar shape and is made of tantalum. Although tantalum is used as the material of the X-ray attenuator 104a in the first embodiment, another material capable of sufficiently shielding the X-rays may be used. Also in the first embodiment, a positional shift $\Delta y$ occurs between an optical path 403 of the X-ray beam refracted through the object 103 and an optical path 402 of the X-ray beam when the object 103 does not exist on the optical path.

Figure 3B:
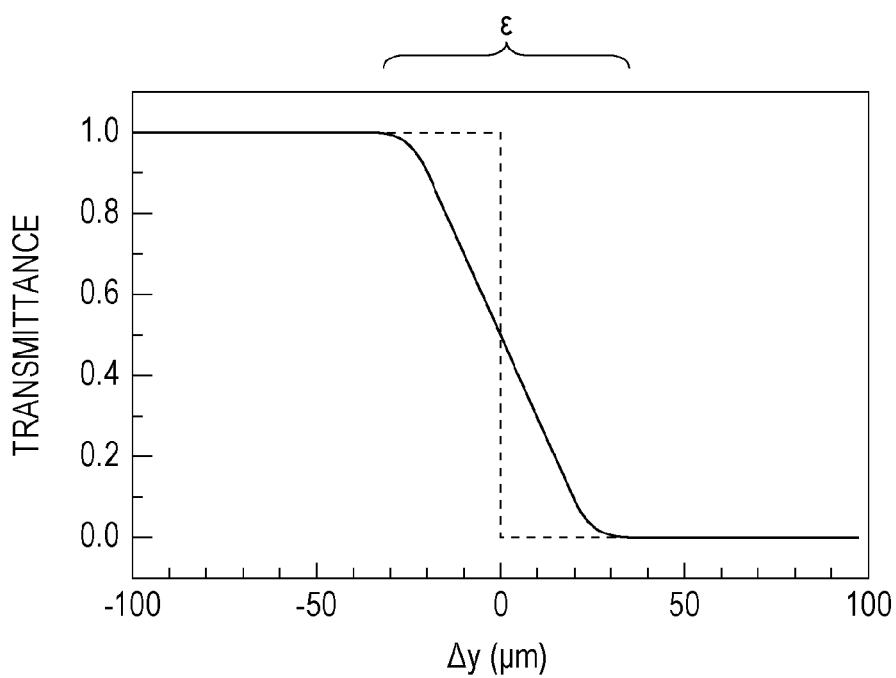
FIG. 3B shows an example of the transmittance of the X-ray attenuator in FIG. 3A.

If the cross-sectional size of the X-ray beam from the X-ray adjuster 102 is very small with respect to the positional shift in the optical path of the X-ray beam, a function $PF(\Delta y)$ is step-shaped, as shown by a broken line in FIG. 3B. However, the positional shift due to the refraction is generally very small. Accordingly, when the cross-sectional size of the X-ray beam is not sufficiently small with respect to the positional shift, the function PF(Δy) has a shape shown by a solid line in FIG. 3B. Consequently, in the X-ray imaging apparatus of the first embodiment, the positional shift ΔY in the Y-axis direction shown in FIG. 3A can be detected in an area indicated by a upward curly bracket with ε in which the transmittance is uniquely varied with respect to the positional shift shown by the solid line in FIG. 3B to calculate the physical quantities concerning the object 103 in the manner described above. The X-ray attenuator 104a in which the amount of attenuation of the X-rays is varied depending on the incident X-rays in Y direction is used in the first embodiment. However, when the amount of refraction in the Z direction orthogonal to both the X and the Y directions is also to be calculated, an X-ray attenuator in which the amount of attenuation of the X-rays is varied depending on the positions in both the Y and the Z directions of the incident X-rays may be used. Alternatively, the X-ray attenuator 104a may be rotated around the X axis (the optical axis of the X-ray imaging apparatus) by 90° for additional measurement.

If the positional shift in the optical path becomes too large, the positional shift is not detected by the X-ray imaging apparatus because no change occurs in the transmittance of X-rays from the X-ray attenuator. In such a case, the use of the result of the detection concerning the X-rays of higher energies, among the results of the detection by the X-ray detector 105, in the calculation in the calculating unit 106 allows the sensitivity to be adjusted to detect the positional shift. This is because the amount of refraction through the object 103 becomes small and the positional shift in the optical path is decreased in the case of the X-rays of higher energies.

A filter (for example, a metal filter or a multilayer mirror) may be arranged on the optical path of the X-ray imaging apparatus to remove the X-rays in energy ranges that are not used in the calculation in the calculating unit 106. The arrangement of the filter between the X-ray source 101 and the object 103 prevents the object 103 from being irradiated with extra X-rays to reduce the radiation damage on the object 103 caused by the X-rays. In order to improve the signal-to-noise (S/N) ratio in the X-ray detector 105, a scattered X-rays removing unit, such as an anti-scattering X-ray grid, capable of removing scattered X-rays may be provided in the X-ray imaging apparatus.

The X-rays of three or more energies may be used in the calculation in the calculating unit 106. In this case, the calculated physical quantities concerning the object 103 may not be constant due to, for example, the effect of noise included in the value $I_2(E)$ detected by the X-ray detector 105. In such a case, for example, a centroid value may be calculated for the collection of the calculated physical quantities to calculate optimal values of the physical quantities.

Second Embodiment

An X-ray imaging apparatus according to a second embodiment of the present invention will now be described with reference to FIG. 4 and FIGS. 5A to 5C.

Figure 4:
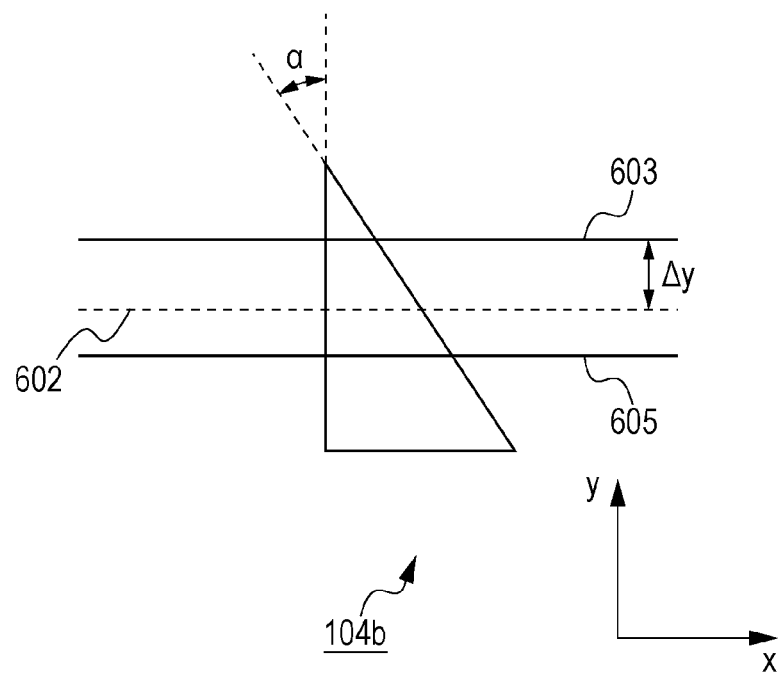
FIG. 4 schematically illustrates an X-ray attenuator according to a second embodiment of the present invention.

The X-ray imaging apparatus of the second embodiment differs from the X-ray imaging apparatus of the first embodiment in that an X-ray attenuator 104b having a cross-sectional shape shown in FIG. 4 is used as the X-ray attenuator 104. The X-ray attenuator 104b is made of stainless steel having X-ray absorption ability. A broken line 602 in FIG. 4 represents the optical path of an X-ray beam when the object 103 does not exist. A thin solid line 603 in FIG. 4 represents the optical path of an X-ray beam refracted through the object 103. In comparison of the optical path lengths of the X-ray beams transmitted through the X-ray attenuator 104b, the optical path length represented by the thin solid line 603 is shorter than that of the broken line 602. In this case, the X-ray beam that is transmitted through the X-ray attenuator 104b on the optical path represented by the thin solid line 603 exhibits an intensity higher than that of the X-ray beam that is transmitted through the X-ray attenuator 104b on the optical path represented by the broken line 602. When the X-ray beam is refracted on an optical path represented by a bold solid line 605, lower intensity is detected due to the difference in the optical path length. The direction in which the positional shift of the optical path can be detected in the second embodiment is the Y-axis direction in FIG. 4 in which the transmittance is varied with respect to the positional shift.

When the X-ray attenuator in which the optical path length of the X-ray beam transmitted through the X-ray attenuator is varied with respect to the positional shift Δy is used, and when the cross-sectional size of the X-ray beam is sufficiently small than the positional shift Δy, the detected value $I_2$ is represented by Equation (8):

$$I_2(E,d)=I_0(E)\cdot\exp\{-t(E)/l_{es}(E,d)\}\cdot\exp\{-l(E)/l_{ep}(E)\} \quad (8)$$

where l denotes the optical path length transmitted through the X-ray attenuator on the optical path of the X-ray beam refracted through the object 103 and $l_{ep}$ denotes the X-ray attenuation length of the material composing the X-ray attenuator 104.

Provided that the apex angle of the X-ray attenuator 104b is denoted by u, as shown in FIG. 4, and the optical path length represented by the broken line 602 of the X-ray beam through the X-ray attenuator 104b is denoted by $l_0$, an optical path length l(E) is represented by Equation (9):

$$l(E)=\tan(\alpha)\cdot\{l_0\cot(\alpha)-\Delta y(E)\} \quad (9)$$

The relationship between positional shift Δy and $I_2$ is represented by Equation (10) by using Equation (8):

$$I_2(E,d)=I_0(E)\cdot\exp\{-t(E)/l_{es}(E,d)\}\cdot\exp[-\tan(\alpha)\cdot\{l_0\cot(\alpha)-\Delta y(E)\}/l_{ep}(E)] \quad (10)$$

The optical path length $l_0$ is calculated according to Equation (11) because the optical path length $l_0$ depends on the apparatus alignment and is measured in a state in which the object 103 does not exist:

$$l_0=-l_{ep}(E)\cdot\ln\{I_2(E)/I_0(E)\} \quad (11)$$

Since the amount of refraction through the object 103 is very small in the actual measurement, it is difficult to set the cross-sectional size of the X-ray beam to a value that is sufficiently smaller than positional shift Δy. In addition, the X-ray beam from the X-ray adjuster 102 has intensity distribution and angle divergence in the cross-sectional direction of the X-ray adjuster 102. Furthermore, the detected value $I_2$ may be affected by, for example, machining error of the X-ray attenuator. The function PF may be corrected in consideration of the effects of the above factors. Alternatively, the function PF(Δy) may be actually measured in a manner described below.

Figure 5A:
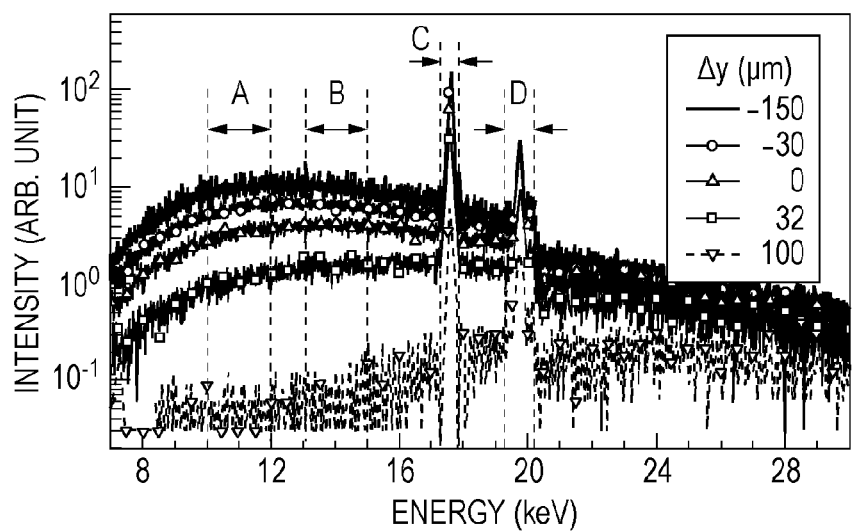
FIG. 5A shows a result of detection by an X-ray detector according to the second embodiment of the present invention.
Figure 5B:
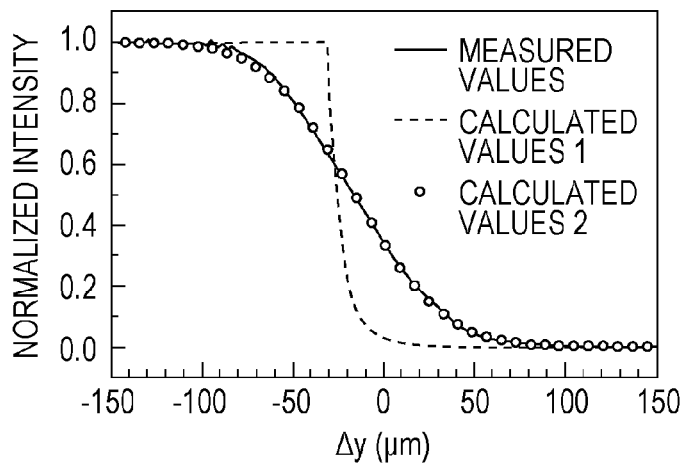
FIG. 5B is a graph representing the PF according to the second embodiment of the present invention.

FIG. 5A shows the intensity information detected by the X-ray detector 105 when the X-ray attenuator 104b is moved (translational scanned) in the Y-axis direction in the case that the object 103 does not exist on the optical path of the X-ray imaging apparatus. The difference of each line in FIG. 5A depends on the amount of change in position of the X-ray attenuator 104b corresponding to the positional shift Δy in FIG. 4. The change of the intensity information concerning certain energy E with respect to the positional shift Δy can be measured to calculate the function PF(Δy). However, since the detected intensities of the X-rays are low in an energy range A in FIG. 5, the S/N ratio of the intensity information may possibly be decreased. In such a case, the function $PF(\Delta y)$ may be calculated from adding up the interval of a certain energy range in the intensity information with respect to the positional shift $\Delta y$. The adding result, as explained above, in the energy range A with respect to the positional shift $\Delta y$ is shown in FIG. 5B as measured values (solid line). The measured values are normalized. Calculated values 1 (broken line) in FIG. 5B denotes a transmittance curve with respect to the positional shift $\Delta y$ when the cross-sectional size of the X-ray beam is much smaller than the positional shift $\Delta y$. FIG. 5B shows that the measured values (solid line) results from extension of the transmittance curve in the direction of the positional shift $\Delta y$. Even when the transmittance curve is extended, as in the above case, the positional shift $\Delta y$ can be acquired from the intensity $I_2$ as long as the intensity is varied with respect to the positional shift and the X-ray attenuator 104b can be used as the X-ray attenuator. The change indicated by the measures values in FIG. 5B corresponds to the function $PF(\Delta y)$. The fitting values for the measured values (solid line) are shown as calculated values 2 (open circles) in FIG. 5B. A fitting function, such as the calculated values 2, capable of satisfactorily representing the measured values may be used as the function $PF(\Delta y)$.

Figure 5C:
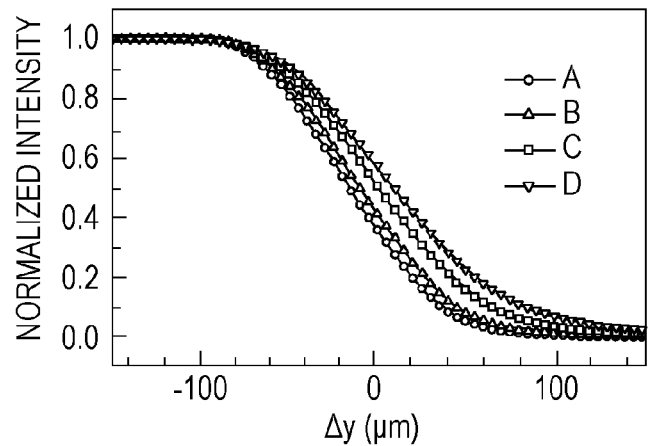
FIG. 5C is a graph representing the PFs according to the second embodiment of the present invention.

FIG. 5C shows the adding results of the energy range A, as same as in FIG. 5B, and of the other energy ranges B to D in FIG. 5A with respect to the positional shift $\Delta y$. The change in each intensity curve shown in FIG. 5C corresponds to the function $PF(\Delta y)$ in each energy range. In other words, the shape of the function $PF(\Delta y)$ also depends on the energy E in the second embodiment i.e. $PF=PF(E, \Delta y)$. Accordingly, Equations (4) and (5) are represented by Equations (12) and (13), respectively:

$$I_2(E,d)=I_0(E)\cdot\exp\{-t(E)/l_{es}(E,d)\}PF(E,\Delta y) \qquad (12)$$

$$\Delta y=PF^{-1}(E,I_2(E,d)/\{I_0\cdot\exp(-t(E)/l_{es}(E,d))\}) \qquad (13)$$

By using the attenuator 104b, since the X-ray detector 105 can detect the change in transmittance even if the optical path is shifted by an amount larger than the amount corresponding to the cross-sectional size of the X-ray beam, the X-ray attenuator 104b of the second embodiment can expand the range of the sensitivity to the positional shift of the optical path, compared to the X-ray attenuator 104a of the first embodiment. When the intensity information detected in the X-ray detector 105 exhibits a good S/N ratio, the adding calculation may not be performed. When the intensity information exhibits a poor S/N ratio, the adding calculation can be performed in the above manner to improve the S/N ratio even if the intensity of the X-rays generated in the X-ray source 101 is low. However, the energy range in which the adding calculation is performed is preferably set to the range in which the difference in the maximum value of the amount of refraction through the object 103 between the energies at both ends of the range does not exceed the divergence angle of the X-ray beam adjusted by the X-ray adjuster 102. The interval is set to the above range in order to decrease the affect of aberration caused by the width of the energies on the image quality.

When the intensity information acquired by performing the adding calculation is used as the intensity information used in the calculation in the calculating unit 106, the attenuation length through the object 103 and the X-ray attenuator 104b is not constant, unlike the case of using monochromatic X-rays. Accordingly, the attenuation length that is corrected in accordance with the energy range in which the adding calculation is performed and the optical path length may preferably be used. However, when the length of the optical path through the object 103 and the X-ray attenuator 104b is short, the attenuation length may be used as a constant value. Particularly, if the ratio of the amount of change in the attenuation length through the object 103 with respect to the median of the attenuation length is smaller than the noise ratio of the intensity information detected by the X-ray detector 105, the attenuation length may be used as a constant value.

The element whose shape (thickness) is varied with the incident position of the X-rays is used as the X-ray attenuator in the second embodiment. However, a device in which the transmittance of the X-rays is varied with the incident position of the X-rays may be used as the X-ray attenuator. For example, a device in which the density distribution or the chemical composition distribution is varied with the incident position of the X-rays may be used as the X-ray attenuator. Specifically, the X-ray attenuator may be composed of two metals differing in the absorption ability of the X-rays and the composition of the two metals may be varied with the incident position of the X-rays. Alternatively, the X-ray attenuator having a porous structure may be used and the size or density of the pores may be varied with the incident position of the X-rays.

Third Embodiment

An X-ray imaging apparatus according to a third embodiment of the present invention differs from the X-ray imaging apparatus of the first embodiment in the X-ray adjuster 102, the X-ray attenuator 104, and the X-ray detector 105. In the third embodiment, an aperture in which multiple pin holes (having a diameter of 60 μm) are two-dimensionally arranged in a shield plate made of tantalum is used as the X-ray adjuster 102. X-ray attenuators as in the first embodiment or the second embodiment that are two-dimensionally arranged are used as the X-ray attenuator 104. Multiple X-ray detectors that are capable of detecting the spectrum distribution of X-rays and that are two-dimensionally arranged are used as the X-ray detector 105.

The X-rays from the X-ray source 101 are divided into multiple X-ray beams in the X-ray adjuster 102 and the X-ray beams are incident on the object 103. The X-ray beams transmitted and refracted through the object 103 are transmitted through the respective X-ray attenuators in the X-ray attenuator 104 and are incident on the respective detectors.

According to the X-ray imaging apparatus of the third embodiment, information on multiple points on the object, corresponding to the number of the X-ray beams divided by the X-ray adjuster 102, can be simultaneously detected by the X-ray detector 105. Accordingly, it is possible for the X-ray imaging apparatus of the third embodiment to measure the object in a shorter time, compared with the X-ray imaging apparatus of the first embodiment or the second embodiment.

Since it is necessary to align the position of the X-ray attenuator 104 with the position of the X-ray detector 105 in a direction orthogonal to the optical axis of the X-ray imaging apparatus in the third embodiment, the X-ray attenuator 104 may be integrated with the X-ray detector 105 without spacing.

Fourth Embodiment

Figure 6:
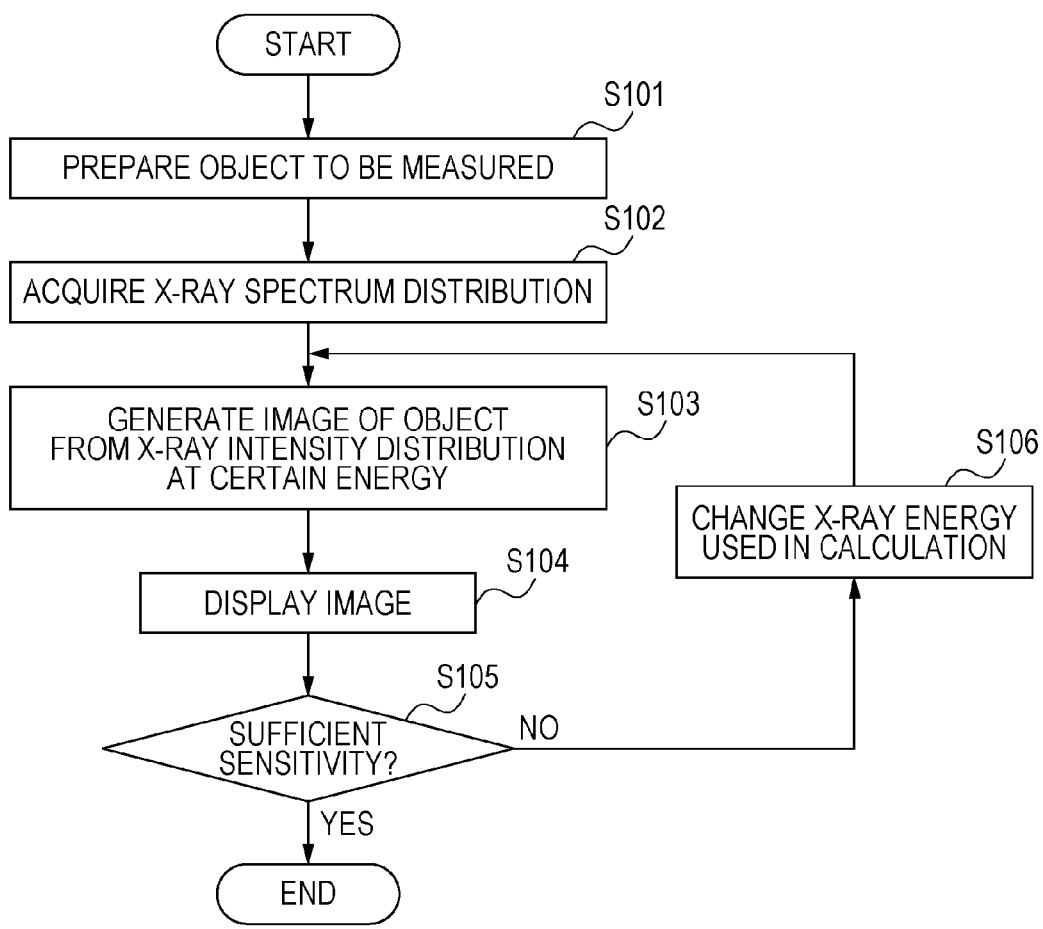
FIG. 6 is a flowchart showing an X-ray imaging method according to a fourth embodiment of the present invention.

An X-ray imaging method according to a fourth embodiment of the present invention using the X-ray imaging apparatus illustrated in FIG. 1 will now be described. FIG. 6 is a flowchart showing the X-ray imaging method according to the fourth embodiment.

Referring to FIG. 6, in Step 101 (hereinafter referred to as S101), the object 103 is prepared and the object 103 is arranged on the stage of the X-ray imaging apparatus. In S102, the object 103 is irradiated with an X-ray beam from the X-ray adjuster 102 and the X-ray beam transmitted through the object 103 and the X-ray attenuator 104 is detected by the X-ray detector 105 to acquire X-ray spectrum distribution. Specifically, the object 103 is scanned with the X-ray beam by moving the stage of the X-ray imaging apparatus to acquire the X-ray spectrum distribution corresponding to each position of the object 103. The X-ray beam may be moved, instead of the stage, to scan the object 103 with the X-ray beam.

In S103, an image of the object is calculated (generated) by the calculating unit 106 on the basis of the intensity information about the X-rays of certain energy, within the X-ray spectrum distribution detected by the X-ray detector 105. In S104, the image of the object is displayed by the display unit 107 on the basis of the result of the calculation in the calculating unit 106. Alternatively, images of the object may be calculated by the calculating unit 106 on the basis of the intensity information about the X-rays of various energies and the images may be displayed in a list by the display unit 107.

In S105, it is determined whether sufficient sensitivity is achieved. If the detection sensitivity is poor and a desired image is not generated, in S106, the energy of the X-rays used in the calculation in the calculating unit 106 is changed to another one within the X-ray spectrum distribution acquired in S102. In S103, an image of the object is calculated (generated) by the calculating unit 106 again on the basis of the intensity information of the X-rays of energy different from the one previously used in S103. In S104, the image of the object is displayed by the display unit 107 on the basis of the result of the calculation. According to the X-ray imaging method of the fourth embodiment, an image can be generated on the basis of any one of the at least two detection results of the X-rays, detected by the detector, to easily adjust the sensitivity to the positional shift of the optical path of the X-ray beam.

Fifth Embodiment

Figure 7:
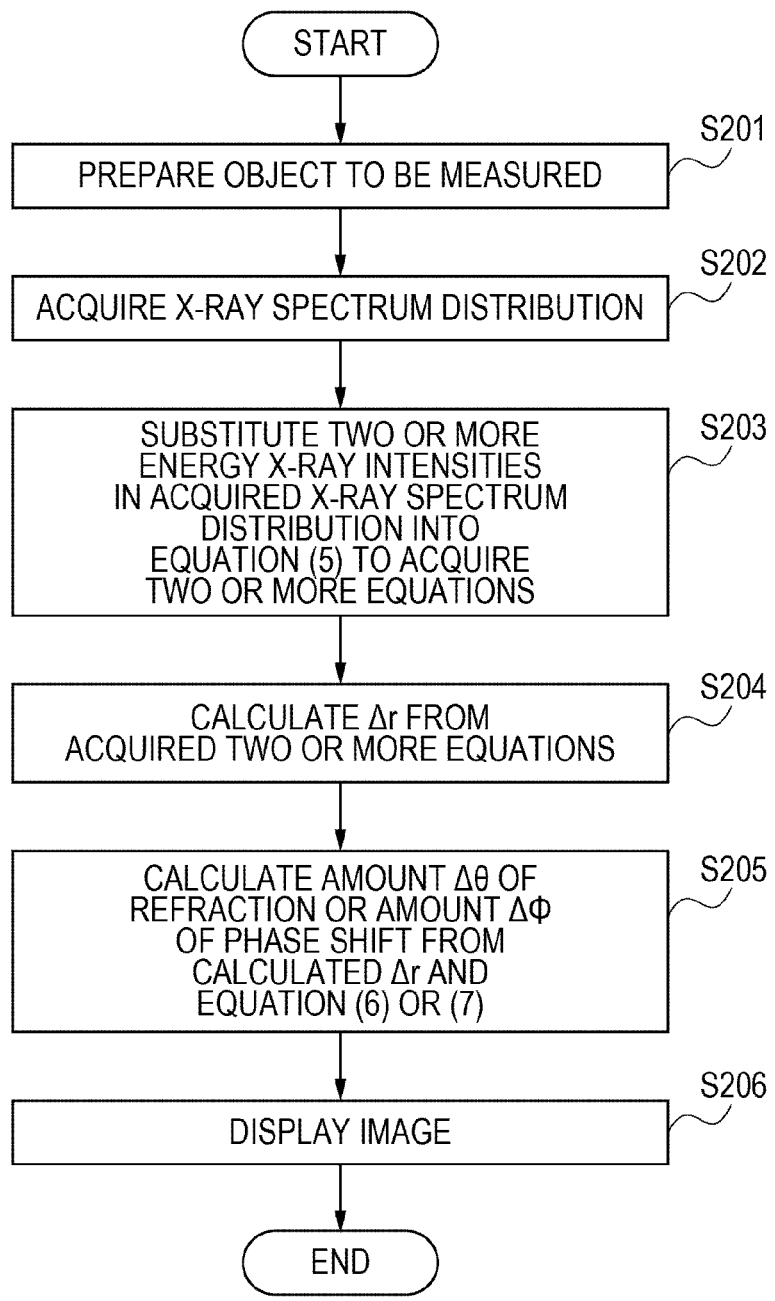
FIG. 7 is a flowchart showing an X-ray imaging method according to a fifth embodiment of the present invention.

Another X-ray imaging method according to a fifth embodiment of the present invention using the X-ray imaging apparatus illustrated in FIG. 1 will now be described. FIG. 7 is a flowchart showing the X-ray imaging method according to the fifth embodiment.

Referring to FIG. 7, in S201, the object 103 is prepared and the object 103 is arranged on the stage of the X-ray imaging apparatus. In S202, the object 103 is irradiated with an X-ray beam from the X-ray adjuster 102 and the X-ray beam transmitted through the object 103 and the X-ray attenuator 104 is detected by the X-ray detector 105 to acquire X-ray spectrum distribution. Specifically, the object 103 is scanned with the X-ray beam by moving the stage of the X-ray imaging apparatus to acquire the X-ray spectrum distribution corresponding to each position of the object 103. The X-ray beam may be moved, instead of the stage, to scan the object 103 with the X-ray beam.

Physical quantities of the object are calculated by the calculating unit 106 on the basis of the intensity information about the X-rays of two or more certain energies, within the X-ray spectrum distribution detected by the X-ray detector 105. Specifically, in S203, the intensity $I_2$ of the X-rays of each of the two or more energies is substituted into Equation (5) to acquire two or more equations. In S204, the positional shift $\Delta r$, the density d of the object, and the thickness t of the object are calculated from the two or more equations. In S205, the amount $\Delta\theta$ of refraction angle or the amount $\Delta\phi$ of phase shift of X-ray is calculated from Equation (6) or Equation (7) by using the positional shift $\Delta r$. In S206, the distributions of the positional shift $\Delta r$, the amount $\Delta\theta$ of refraction angle, and the amount $\Delta\phi$ of phase shift calculated at each position of the object may be displayed by the display unit 107. According to the X-ray imaging method of the fifth embodiment, it is possible to easily extract the amount of refraction of the X-rays through the object 103 even if the absorption of the X-rays through the object 103 is not negligible.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-102527, filed Apr. 27, 2010, which is hereby incorporated by reference herein in its entirety.

REFERENCE SIGNS LIST

101 X-ray source
102 X-ray adjuster
103 object to be measured
104 X-ray attenuator
105 X-ray detector
106 calculating unit
107 display unit

The invention claimed is:

1. An X-ray imaging apparatus irradiating an object to be measured with an X-ray beam from an X-ray source that generates X-rays of a first energy and X-rays of a second energy different from the first energy to measure an image of the object to be measured, the X-ray imaging apparatus comprising:
   an attenuator configured to attenuate the X-ray beam transmitted through the object to be measured; and
   a detector including a pixel configured to detect the X-ray beam transmitted through the attenuator,
   wherein the attenuator is configured so as to vary an amount of attenuation of the X-rays depending on a position on which the X-ray beam is incident in an area corresponding to the pixel,
   wherein an intensity of the X-ray beam detected by the pixel varies depending on the position on which the X-ray beam is incident in the area corresponding to the pixel, and
   wherein the detector is configured so as to detect the X-rays of the first energy and the X-rays of the second energy.

2. The X-ray imaging apparatus according to claim 1, wherein the detector is a spectroscope detecting spectrum distribution of the X-ray beam.

3. The X-ray imaging apparatus according to claim 1, further comprising:
   a control unit configured to generate the image on the basis of either of the result of the detection of the X-rays of the first energy and the result of the detection of the X-rays of the second energy, detected by the detector, to adjust sensitivity of the X-ray imaging apparatus.

4. The X-ray imaging apparatus according to claim 3, wherein the detector has an energy resolution sufficient to discriminately detect the intensity of the X-rays of each of the first energy and the second energy.

5. The X-ray imaging apparatus according to claim 4, further comprising:

a calculating unit configured to calculate a positional shift of the X-ray beam through the object to be measured on the basis of the result of the detection of the X-rays of the first energy and the result of the detection of the X-rays of the second energy, detected by the detector.

6. The X-ray imaging apparatus according to claim 5, further comprising:
a calculating unit configured to calculate a positional shift of the X-ray beam through the object to be measured on the basis of the result of the detection of the X-rays of the first energy or the result of the detection of the X-rays of the second energy, detected by the detector.

7. The X-ray imaging apparatus according to claim 1, wherein the attenuator is configured to vary an X-ray transmittance in the area.

8. The X-ray imaging apparatus according to claim 1, wherein the area corresponds to the pixel on a one-to-one basis.

9. The X-ray imaging apparatus according to claim 1, wherein the detector includes a plurality of pixels.

10. The X-ray imaging apparatus according to claim 9, wherein the attenuator includes a plurality of areas.

11. The X-ray imaging apparatus according to claim 9, further comprising a plurality of attenuators.

12. The X-ray imaging apparatus according to claim 1, wherein the attenuator is configured to indicate a different X-ray attenuation amount with respect to a different $\Delta r$, where $\Delta r$ denotes a distance of a positional shift due to transmission through the object to be measured.

13. The X-ray imaging apparatus according to claim 6, wherein the calculating unit is configured to calculate the positional shift of the X-ray beam through the object to be measured using an equation indicating a relation between the positional shift of the X-ray beam through the object to be measure, an X-ray intensity of the X-ray beam in a case where the X-ray beam is not transmitted through the object to be measured, and an X-ray intensity of the X-ray beam in a case where the X-ray beam is transmitted through the object to be measured.

14. The X-ray imaging apparatus according to claim 4, wherein the calculation unit is configured to calculate the positional shift of the X-ray beam through the object to be measured by using a simultaneous equation consisting of a first equation obtained by substituting an X-ray intensity of the first energy into an equation indicating a relation between the positional shift of the X-ray beam due to transmittance through the object to be measured, the X-ray intensity of the X-ray beam in a case where the X-ray beam is not transmitted through the object to be measured, and the X-ray intensity of the X-ray beam in a case where the X-ray beam is transmitted through the object to be measured, and a second equation obtained by substituting an X-ray intensity of the second energy into the equation indicating the relation between the positional shift of the X-ray beam due to transmittance through the object to be measured, the X-ray intensity of the X-ray beam in a case where the X-ray beam is not transmitted through the object to be measured, and the X-ray intensity of the X-ray beam in a case where the X-ray beam is transmitted through the object to be measured.

15. The X-ray imaging apparatus according to claim 1, wherein the attenuator is configured to monotonically increase or decrease the transmittance when the position on which the X-ray beam is incident in the area is changed in a first direction.

* * * * *